(12) United States Patent
Powers et al.

(10) Patent No.: US 6,980,859 B2
(45) Date of Patent: Dec. 27, 2005

(54) AUTOMATED EXTERNAL DEFIBRILLATOR WITH A PLURALITY OF POWER SOURCES

(75) Inventors: Daniel J. Powers, Issaquah, WA (US); Gregory Dean Brink, Bainbridge Island, WA (US); Anthony G. Picardo, Tacoma, WA (US); Dennis Eugene Ochs, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 482 days.

(21) Appl. No.: 10/104,223

(22) Filed: Mar. 22, 2002

(65) Prior Publication Data

US 2003/0181950 A1     Sep. 25, 2003

(51) Int. Cl.⁷ .................................................. A61N 1/18
(52) U.S. Cl. ............................................................ 607/5
(58) Field of Search ........... 307/85; 320/114; 607/2–8, 607/29

(56) References Cited

U.S. PATENT DOCUMENTS

| | | | |
|---|---|---|---|
| 4,096,856 A | * | 6/1978 | Smith et al. .................... 607/5 |
| 4,635,639 A | * | 1/1987 | Hakala et al. .................. 607/4 |
| 5,224,870 A | * | 7/1993 | Weaver et al. ............... 439/157 |
| 5,658,316 A | * | 8/1997 | Lamond et al. ................. 607/5 |
| 5,983,137 A | * | 11/1999 | Yerkovich ........................ 607/5 |
| 6,083,246 A | * | 7/2000 | Stendahl et al. ................ 607/5 |
| 6,128,530 A | * | 10/2000 | Galen et al. ..................... 607/5 |
| 6,223,077 B1 | * | 4/2001 | Schweizer et al. ............. 607/5 |
| 6,577,102 B1 | * | 6/2003 | Vaisnys et al. ............. 320/114 |
| 6,586,850 B1 | * | 7/2003 | Powers ......................... 307/85 |

* cited by examiner

*Primary Examiner*—Mark Bockelman
(74) *Attorney, Agent, or Firm*—Tony Piotrowski

(57) ABSTRACT

An automated or semi-automated external defibrillator (AED) is provided with a plurality of power sources. The AED includes a first power source that powers circuitry creating a defibrillation electrical shock, and a second power source for powering other circuitry. By including a separate power source for the low-power needs of the AED, the high-power source will typically last longer than if the low-power source were omitted. This reduces maintenance costs, particularly where the high-power source is more expensive to replace than the low-power source. Furthermore, one may use the high-power source as a backup to the low-power source so the AED can still operate even if the low-power source fails.

23 Claims, 9 Drawing Sheets

AUTOMATED EXTERNAL DEFIBRILLATOR WITH A PLURALITY OF POWER SOURCES

FIELD OF THE INVENTION

The present invention is directed generally to electronic devices, and more particularly an automated or semi-automated external defibrillator (AED) with a plurality of power sources. For example, the AED can use one power source to power the AED's shock generation circuit and another power source to operate the AED's processor circuit.

BACKGROUND

Sudden cardiac arrest (SCA) is one of the leading causes of death in North America. But unlike other health problems of this magnitude, SCA is treatable. The treatment for most cases of SCA is immediate treatment with a defibrillator, a device that shocks the heart out of a fatal rhythm, allowing a normal, healthy rhythm to resume. Science and industry have developed an automated or semi-automated external defibrillator (collectively referred to as an "AED") that provides a safe and effective treatment, and is automated enough to be used by non-medical personnel. AEDs can be placed at dispersed, non-hospital locations throughout a community to provide victims of SCA quick access to this treatment. For example, AEDs are now being placed in a wide range of settings such as clinics, offices and industrial locations, airports and airplanes, health clubs and golf courses.

An AED is a portable battery-operated device that analyzes a patient's heart rhythm, and, if appropriate, administers an electrical defibrillation shock (automated) or instructs an operator to administer the shock (semi-automated) to the patient via electrode pads. For example, such a defibrillator shock can often revive a patient who is experiencing ventricular fibrillation (VF).

AEDs typically require two levels of power to operate properly. An AED requires a high level of power generating a defibrillation shock, and a low level of power to operate circuitry, such as a microprocessor, while the AED is in use or during periodic—typically daily—self-testing while the AED is not in use. The high-power requirement is typically met using relatively expensive lithium batteries, which provide good power density (watts per cubic centimeter), the ability to deliver high-power pulses when needed, and a long shelf life. The low-power requirements can also be met from the lithium batteries. However, using the lithium batteries to power the microprocessor during self-testing may slowly discharge the batteries, thus shortening life and increasing field maintenance requirements by shortening the battery-replacement interval.

SUMMARY

In one embodiment of the invention, an AED is provided that includes a first power source that powers circuitry creating a defibrillation electrical shock, and a second power source for powering other circuitry. By including a separate power source for the low-power needs of the AED, the high-power source will typically last longer than if the low-power source were omitted. This reduces maintenance costs, particularly where the high-power source is more expensive to replace than the low-power source. Furthermore, one may use the high-power source as a backup to the low-power source so the AED can still operate even if the low-power source fails.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

DETAILED DESCRIPTION

The following discussion is presented to enable a person skilled in the art to make and use the invention. Various modifications to the embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. Furthermore, for purposes of the application, "a self-contained power source" is a power source, such as a battery, fuel cell, or solar cell, that can provide power without a connection to power mains such as an AC outlet. Additionally, reference is collectively made to "an automated or semi-automatic external defibrillator (AED)". This reference describes a class of external defibrillators, where the shock is either delivered by the defibrillator automatically without specific user action, or semi-automatically with the user action generally limited to pushing a shock delivery button upon instruction or authorization from the defibrillator. The reference is not intended to be in the alternative.

Figure 1:
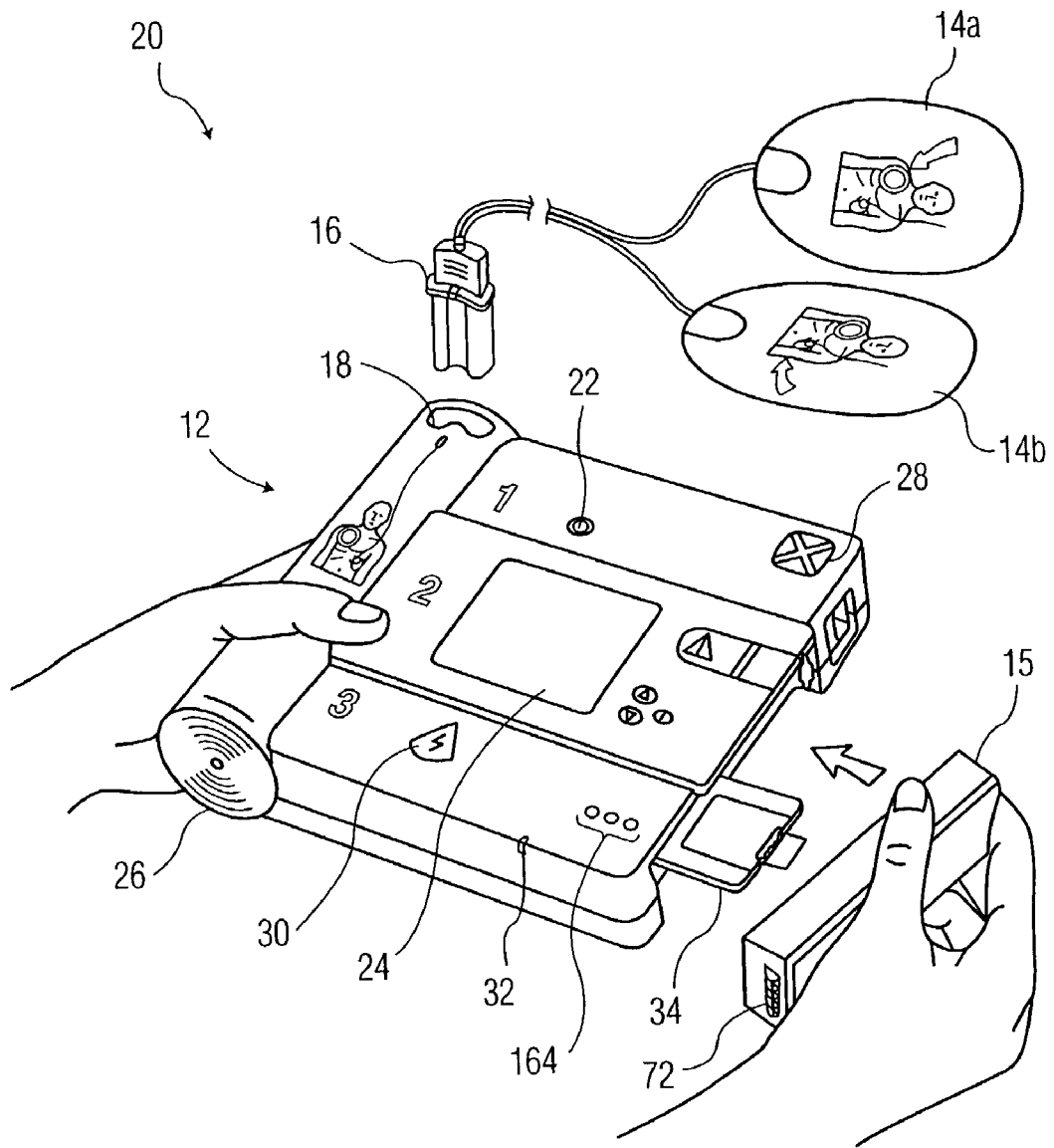
FIG. 1 is a perspective view of an AED system, according to an embodiment of the invention.

FIG. 1 is a perspective view of an AED system 20 according to an embodiment of the invention. The AED system 20 includes an AED 12 for generating a defibrillation shock, defibrillator electrode pads 14a and 14b for providing the shock to a patient, and a power-source cassette 15. The power-source cassette 15 includes electrical contacts 72 that connect with corresponding electrical contacts (not shown) within the AED 12 upon insertion of the power-source cassette 15 into the AED 12. A connector 16 couples the electrode pads 14a and 14b to a receptacle 18 of the AED 12. Typically, the electrode pads 14a and 14b are sealed within a flexible, i.e., soft, package (not shown) that an operator (not shown) tears or peels open to access the electrode pads 14a and 14b. The package acts as a moisture barrier that prevents the electrode-pad contact gel from prematurely drying out during storage of the electrode pads 14a and 14b.

The power-source cassette 15 includes a source of relatively high power so that the AED 12 can quickly generate and deliver a defibrillation shock, and includes a relatively low-power source that powers AED circuitry having lower-power requirements. For example, the low-power circuitry typically includes a microprocessor that controls the operation of the AED 12 during its use to resuscitate a patient and performs periodic self-tests which the AED 12 is in storage. For example, the microprocessor periodically checks the high- and low-power sources in the cassette, and sounds an alarm if they need replacing. Because the cassette 15 includes a low-power source to power the AED 12 during such low-power operations, the high-power source, which is typically more expensive than the low-power source, lasts longer than it would in an AED with no low-power source. This reduces the frequency at which one replaces the cassette 15, and thus reduces maintenance costs.

The AED 12 includes a main on/off key switch 22, a display 24 for displaying operator instructions, cardiac waveforms, or other information, a speaker 26 for providing audible operator instructions or other information, an AED status indicator 28, and a shock button 30, which the operator presses to deliver a shock to the patient. The AED 12 may also include a microphone 32 for recording the operator's voice and other audible sounds that occur during the rescue, and a data card 34 for storing these sounds along with the patient's ECG and a record of AED events for later study.

Still referring to FIG. 1, during an emergency where it is determined that the patient may need a shock, the operator retrieves the AED 12 and installs the power-source cassette 15 if it is not already installed. Next, the operator removes the electrode pads 14a and 14b from the protective package and inserts the connector 16 into the receptacle 18. Then, the operator turns the on/off switch 22 to the "on" position to activate the AED 12. Following the instructions displayed on the display 24 or "spoken" via the speaker 26, the operator places the electrode pads 14a and 14b on the patient in the respective positions shown in the pictures on the pads and on the AED 12. After the operator places the electrode pads 14a and 14b on the patient, the AED 12 analyzes the patient's ECG to determine whether the patient is suffering from a shockable heart rhythm. If the AED 12 determines that the patient is suffering from a shockable heart rhythm, then it instructs the operator to depress the shock button 30 to deliver a shock to the patient. Conversely, if the AED 12 determines that the patient is not suffering from a shockable heart rhythm, it informs the operator to seek appropriate non-shock treatment for the patient and often disables the shock button 30 so that even if the operator presses the button 30, the AED 12 does not shock the patient.

Because the AED 12 must be ready to perform in an emergency, it performs periodic self-tests and provides notice of the results if appropriate. For example, AED 12 periodically tests its power supplies, and provides an alarm when the cassette needs replacement because its power-delivering capabilities have fallen below a predetermined standard. The alarm is provided using the display 24, speaker 26, status indicator 28, and/or LEDs 164. In response to this alarm, one replaces the power-source cassette 15.

Figure 2:
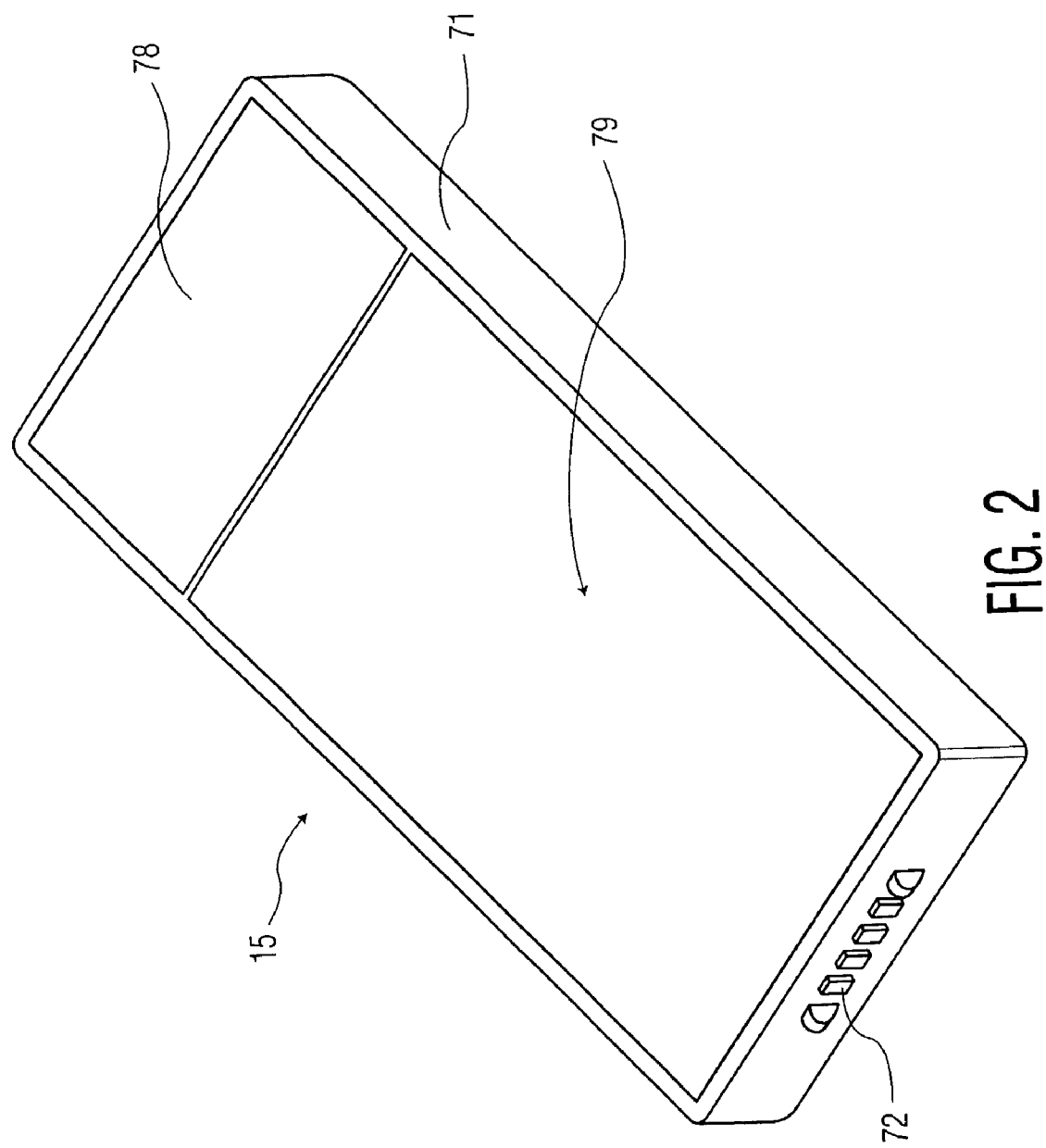
FIG. 2 is a perspective view illustrating a dual-power-source cassette with no user access, according to an embodiment of the invention.
Figure 3:
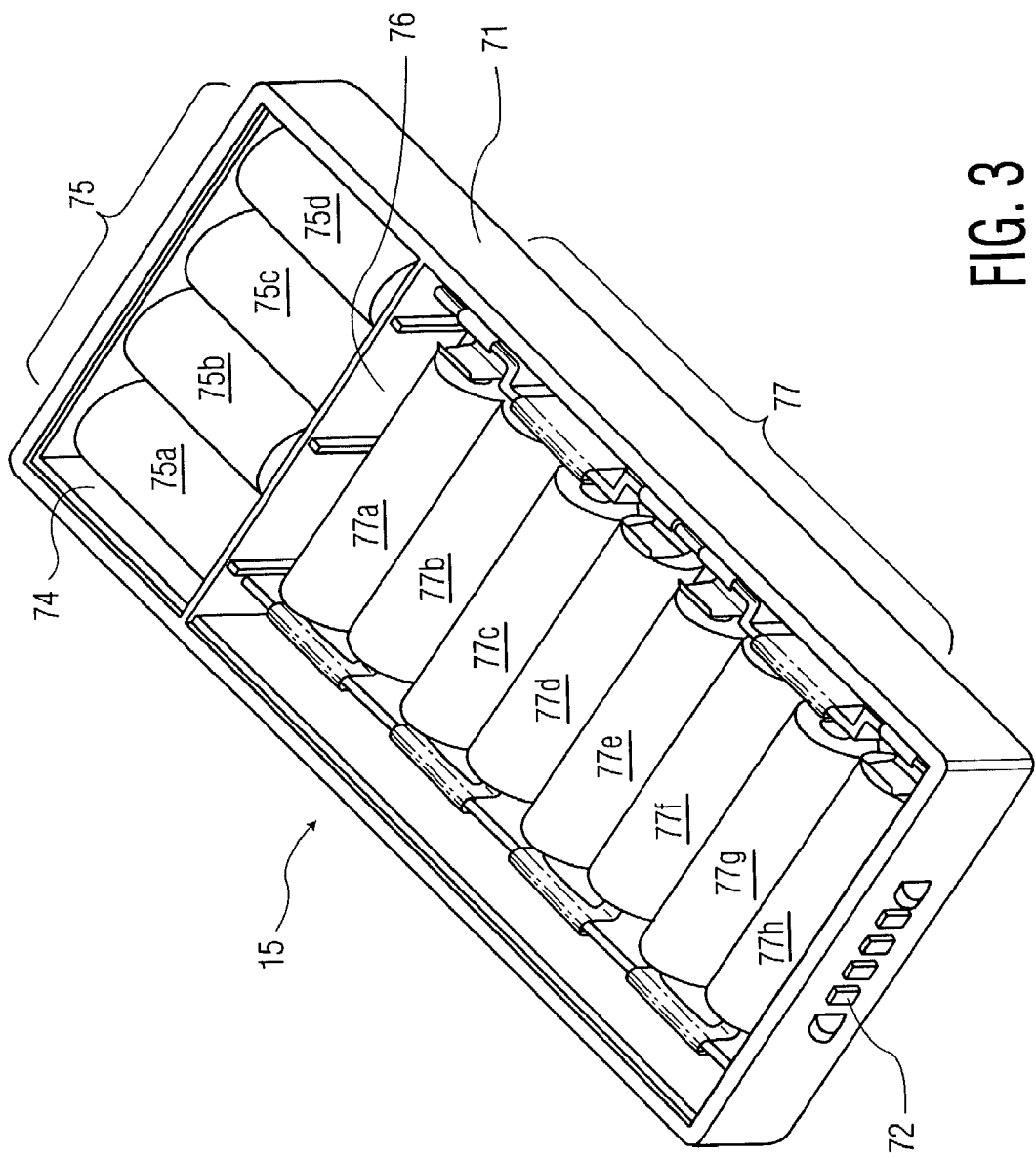
FIG. 3 is a perspective view of FIG. 2 illustrating the dual-source cassette with its cover removed to reveal the dual-power sources.

FIGS. 2 and 3 are perspective views illustrating a dual-power-source cassette 15 that allows no user access in accordance with an embodiment of the invention. FIG. 2 illustrates the cassette 15 with its cover in place, and FIG. 3 illustrates the cassette 15 with its cover removed to reveal the dual-power sources. Referring to FIG. 2, cassette 15 includes a cassette body 71, contacts 72, a high-power-source compartment cover 78, and a low-power-source compartment cover 79. The cover 78 and the cover 79 are both sealed to the cassette body 71. No provision is made for user replacement of the power sources. That is, when at least one of the high-power or low-power sources fails, the entire cassette 15 is replaced.

FIG. 3 illustrates the dual-power-source cassette 15 of FIG. 2 with the cover 78 and cover 79 removed. The cassette 15 includes a high-power-source compartment 74 for housing a high-power source 75, illustrated as batteries 75a–d, and a low-power-source compartment 76 for housing a low-power source 77, illustrated as batteries 77a–h. In one embodiment, the high-power-source batteries 75a–d are lithium batteries, and the low-power-source batteries 77a–h are alkaline batteries. Although shown as batteries, the power sources may include other sources of power such as a fuel cell. Although the high-power-source batteries 75a–d are shown coupled in parallel, and low-power-source batteries 77a–h are shown coupled in series, the batteries 75a–d and 77a–h may be coupled in any manner that delivers the voltage and power required by the AED 12.

As discussed above, providing dual-power sources to the AED 12 typically reduces maintenance frequency and expenses by extending the life of cassette 15. For example, assuming that the batteries 75 are lithium batteries, and that the AED 12 delivers fewer than about 20 shocks with these batteries. If the batteries 75 are also used to power the AED 12 during daily self-tests, their lifetime is about three years. But by including the batteries 77 to power the AED 12 during these self-tests, the life of the batteries 75 can be extended, for example to about five years in one embodiment. Assuming that the batteries 77 have a similar lifetime, the lifetime of the cassette 15 is similarly increased. And also assuming that the batteries 77 are alkaline or other low-cost batteries, this increase in lifetime comes with a small increase in the cost of the cartridge 15.

Figure 4:
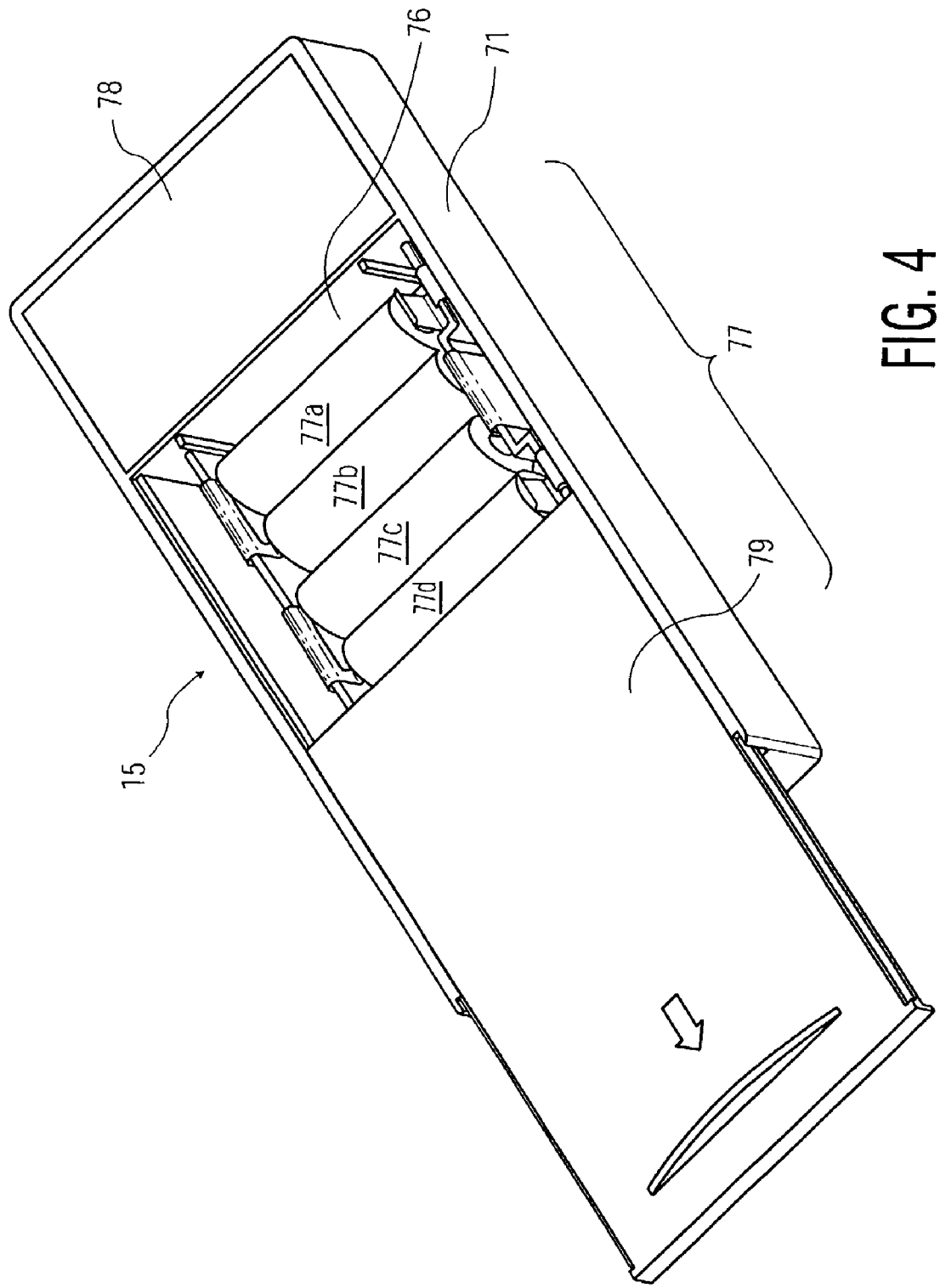
FIG. 4 is a perspective view illustrating a dual-power-source cassette with a serviceable low-power source, according to an embodiment of the invention.

FIG. 4 illustrates the cassette 15 of FIG. 1 having a replaceable low-power source, in accordance with an embodiment of the invention. Specifically, the cassette 15 of FIG. 4 is similar to the cassette 15 of FIGS. 2 and 3 except that the cover 79 is removable to allow one to replace the low-power batteries 77a–h. This may further extend the life of the cassette 15 since one can replace the relatively low-cost batteries 77 when necessary, and replace the cassette 15 only when the high-power batteries 75 fail. This may further reduce maintenance frequency and cost, particularly because batteries 77 routinely fail before batteries 75.

Figure 5:
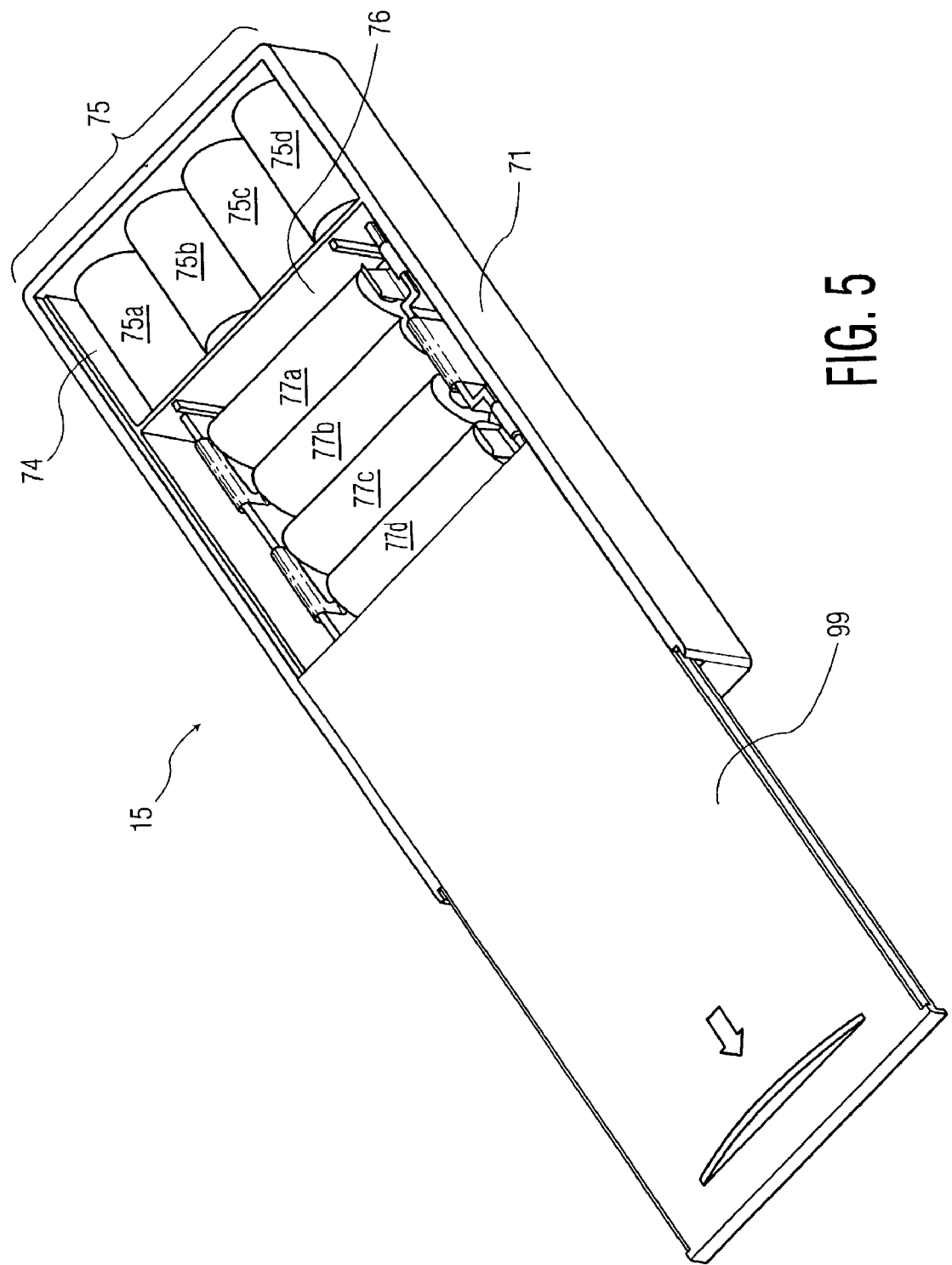
FIG. 5 illustrates a dual-power-source cassette with serviceable low-and high-power sources, according to an embodiment of the invention.

FIG. 5 illustrates a cassette 15 with serviceable power sources, according to an embodiment of the invention. That is, the cassette 15 is similar to the cassette 15 of FIG. 4, except both the high- and low-power sources are replaceable. Specifically, cassette 15 includes a power-source compartments cover 99 that is arranged to be removable for replacement of both the high-power source 75, illustrated as batteries 75a–d, and the low-power source 77, illustrated as low-power batteries 77a–h. This may further reduce maintenance frequency and costs by allowing one to replace only the batteries 75, and not replace the entire cassette 15 when the batteries 75 fail.

Figure 6:
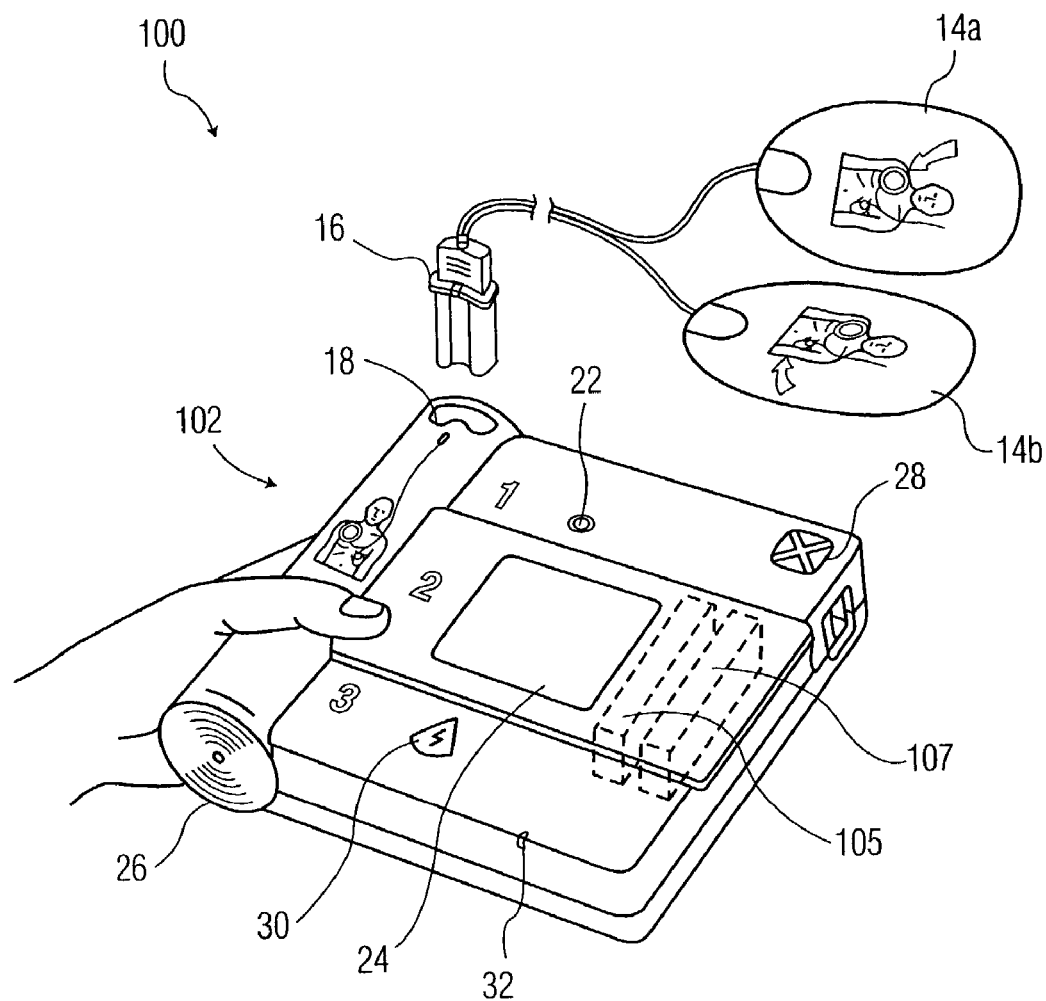
FIG. 6 is a perspective view illustrating an AED system where both the high- and low-power sources are individually and removably carried within the AED, according to an embodiment of the invention.

FIG. 6 is a perspective view of an AED system 100 where both the high- and low-power sources are individually and removably carried within the AED, in accordance with an embodiment of the invention. The AED system 100 includes a dual-power source AED 102, which individually and removably carries both the high-power source, illustrated as batteries 105, and low-power source, illustrated as batteries 107, internally in a power-source compartment having a cover. The AED system 100 is otherwise substantially similar in construction and operation to the AED system 20 described in conjunction with FIG. 1. The high-power batteries 105 provide the AED 102 with a high-power source that powers circuitry generating a defibrillation shock. The low-power batteries 107 provide a low-power source that powers circuitry other than the circuitry generating a defibrillation shock. Because the batteries 105 and 107 can be separately replaced when appropriate, the AED system 100 provides the same reduction in maintenance frequency and cost as discussed above in conjunction with FIG. 5.

Figure 7:
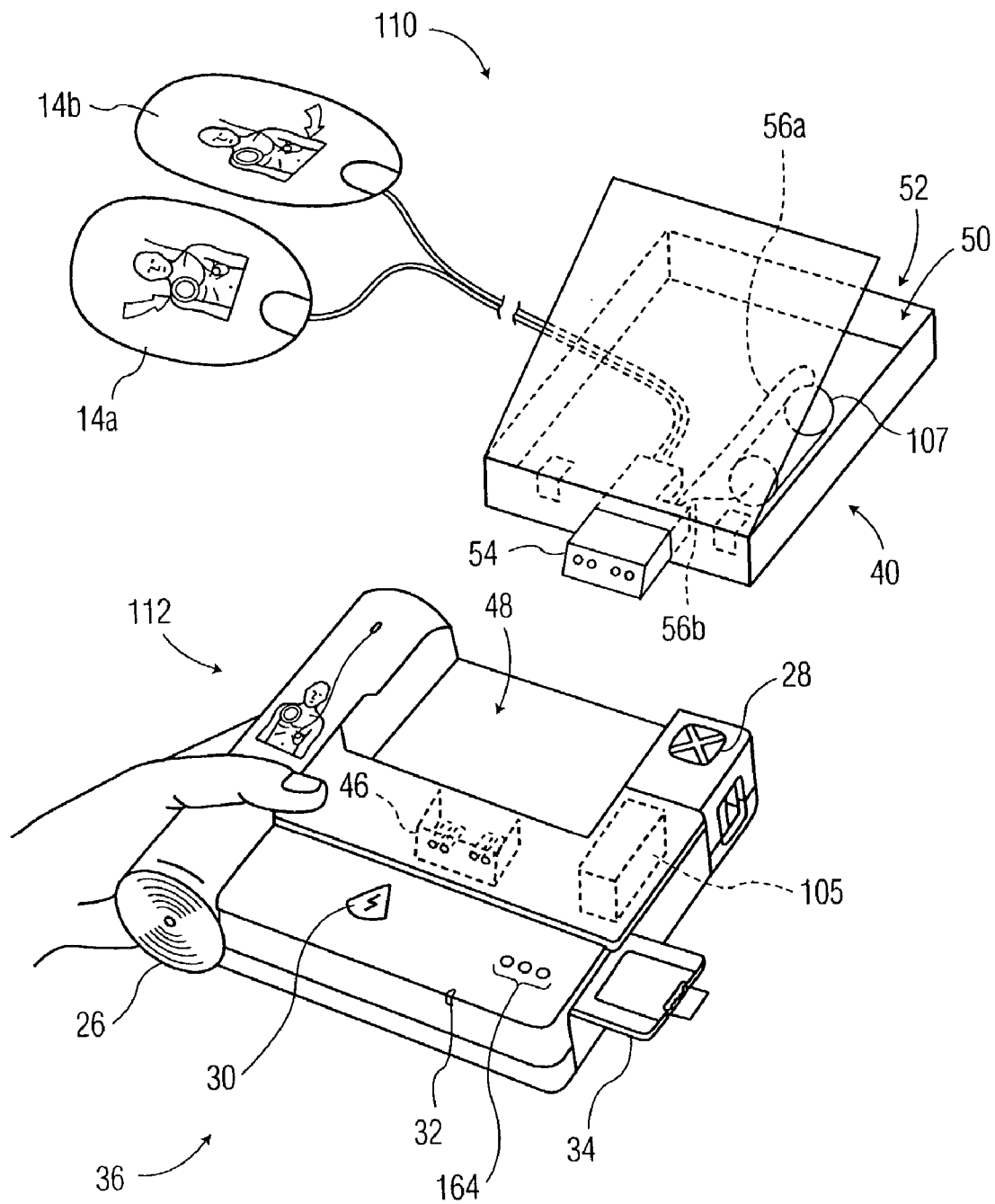
FIG. 7 is a perspective view illustrating an AED system that includes an AED having an internal high-power source and a pad cartridge containing a low-power source and electrode pads, according to an embodiment of the invention.

FIG. 7 is a perspective view of an AED system that includes an AED having an internal high-power source and a pad cartridge containing a low-power source, in accordance with an embodiment of the invention. Specifically, an AED system 110 includes an AED 112, a high-power source 105, pad/power source cartridge 40, and low-power source 107. The AED system 110 is arranged and operates substantially similar to AED system 100 of FIG. 6, except the low-power source 107 is located in the cartridge 40, and not within the AED 112.

The cartridge 40 includes a compartment 50 for storing the electrode pads 14a and 14b and the low-power-source battery 107, a lidded housing 52 that defines the compartment 50, a connector 54 that mates with the connector 46 when the housing 52 is disposed within a receptacle 48, and leads 56a and 56b that connect the battery 107 to the connector 54. For clarity in the illustration, the on/off switch 22 and display 24 are omitted from FIG. 9. To accommodate the connector 46 and receptacle 48, the switch 22 and the display 24 may be displaced from their respective locations on the AED 12 of FIG. 1.

In one embodiment, the battery 107 is a low-cost, disposable battery such as a zinc-carbon, zinc-mercury, or zinc-manganese, i.e., alkaline, battery. Such a battery has been found to have approximately the same shelf life as the pads 14a and 14b and to degrade with temperature at a rate that is similar to the pads' temperature-degradation rate. Therefore, as discussed below, when the pads 14a and 14b need replacing, the battery 107 typically needs replacing, and visa-versa. Therefore, maintenance frequencies can typically be reduced by replacing the entire cartridge 40 instead of separately replacing the pads and the battery. Moreover, the battery 107 may or may not be replaceable independently of the cartridge 40, and although one battery 107 is shown, the cartridge may store multiple batteries 107 coupled in either series or parallel. Cartridges similar to the cartridge 40 (except without the battery 107) are discussed in U.S. patent application Ser. No. 09/852,431, entitled CARTRIDGE FOR STORING AN ELECTRODE PAD AND METHODS FOR USING AND MAKING THE CARTRIDGE, which is incorporated by reference.

In operation of the embodiment illustrated in FIG. 7, one periodically replaces a single component—the cartridge 40—in the field to maintain the AED system 110. That is, one replaces the cartridge 40 at regular intervals to maintain a viable set of pads 14a and 14b and an adequate charge level on the low-power source 107. Therefore, by allowing routine field maintenance with the replacement of a single component, the AED system 110 is relatively simple to maintain. Furthermore, because, as discussed above, the battery 107 typically costs on the order of $1/100^{th}$ of what the battery 105 costs, including the low-power-source battery 107 in the cartridge 40 reduces the cost of maintaining the system 110. In an alternative embodiment, the replacement cartridge 40 may omit the battery 107, and allow the person performing the maintenance to purchase and install a fresh low-power-source battery 107.

In one embodiment, one replaces the original cartridge with a replacement cartridge 40 when the pads 14a and 14b need replacement either because they have been used or because their shelf life has expired. As long as the battery 107 has a life that is at least as long as the pads' shelf life, one will typically replace the cartridge 40 before the battery 107 loses its ability to provide adequate power.

In another embodiment, one replaces the original cartridge with a replacement cartridge 40 when the low-power-source battery 107 needs replacement. Specifically, the AED 12 monitors the low-power-source battery 107 and the high-power-source battery 105, and provides a notification when the charge level on either falls below a predetermined standard. As long as the pads 14a and 14b have a life that is-at least as long as the low-power-source battery's 107' expected life, then one will typically replace the cartridge 40 before the pads expire. Furthermore, as stated above, some types of batteries such as alkaline batteries degrade with exposure to heat at a rate similar to the rate at which the pads 14a and 14b degrade with exposure to heat. Therefore, by using such a battery for the battery 107, the AED 112 can provide a warning if one should replace the cartridge 40 earlier than scheduled due to heat degradation of the pads 14a and 14b.

Figure 8:
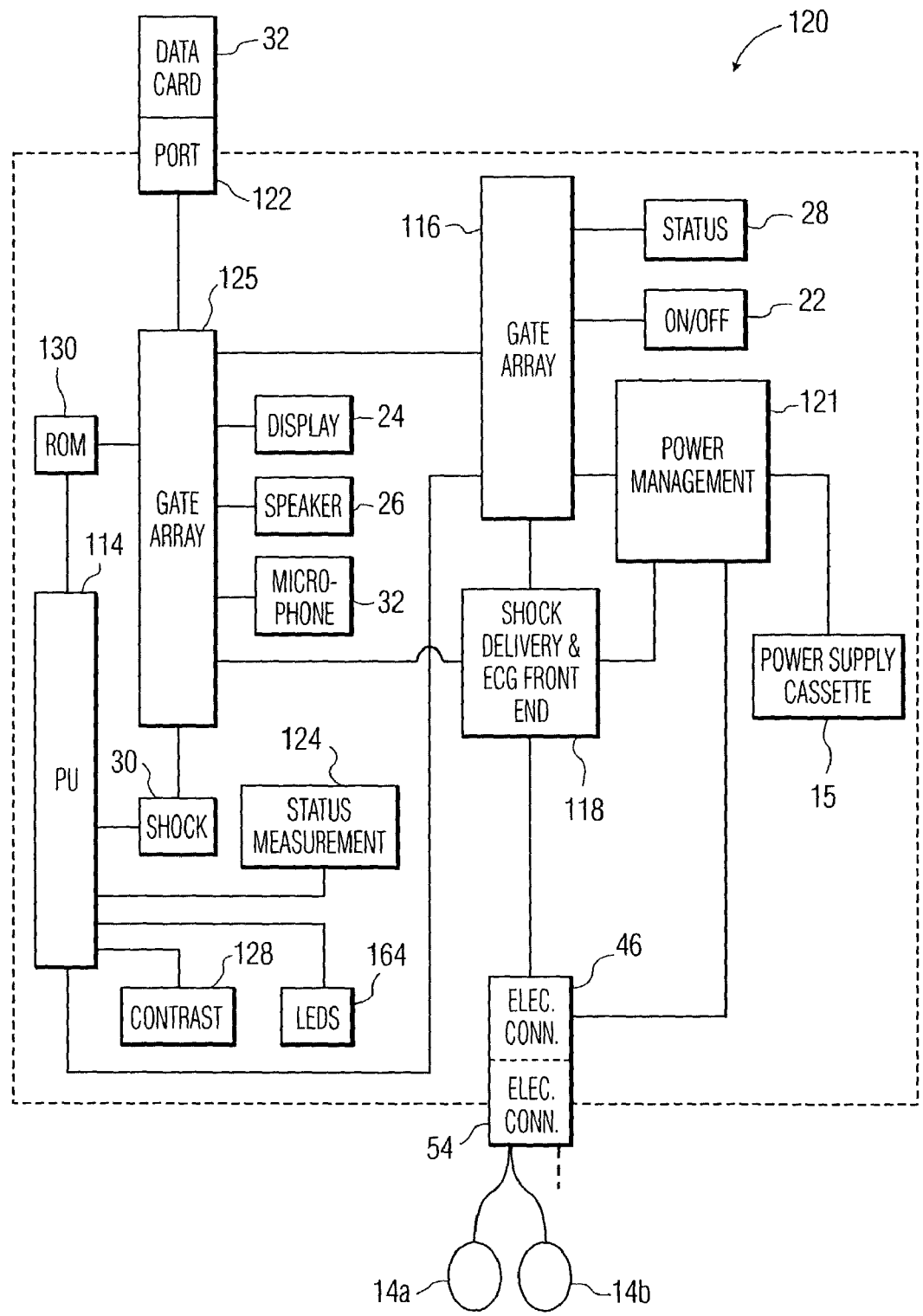
FIG. 8 is a schematic block diagram of the circuitry of the AEDs of FIGS. 1, 6, and 7, according to an embodiment of the invention.

FIG. 8 is a schematic circuit block diagram 120 of the circuit that the AEDs 12, 102, and 112 of FIGS. 1, and 6–7, respectively, can incorporate according to an embodiment of the invention. For clarity, the block diagram 120 is discussed in conjunction with the AED 12, it being understood that the discussion also generally applies to AED's 102, and 112 unless otherwise noted.

The circuit 120 includes a power-management (PM) circuit 121, which interfaces with a processing unit (PU) 114 via a gate array 116, a circuit 118 for creating a defibrillation electrical shock, delivery, an ECG front-end, and the power-supply cassette 15. The power sources within the supply 15 can also be carried internally to the AED 12 as illustrated in FIG. 6, or carried partially internally and partially in a pad/power-source cartridge as illustrated in FIG. 7. Under the control of the PU 114, the PM circuit 121 distributes power from the power cassette 15 to the other circuits of the AED 12. In addition, the PU 114 monitors the voltage across the power supplies within the cassette 15 via the PM 121 and creates an alarm via the display 24, speaker 26, status indicator 28, LEDs 164, or other means to indicate that at least one of the power sources needs to be replaced.

The AED 12 also includes the circuit 118 for generating and delivering a defibrillation shock, and for operating the ECG front-end; which, during treatment of a patient (not shown), samples the patient's ECG to determine if the patient is suffering from a shockable heart arrhythmia. The PU 114 receives the samples from the circuit 118 via a gate array 125 and analyzes them. If analysis indicates that the patient is suffering from a shockable heart rhythm, then the PU 114 instructs the circuit 118 via the gate array 125 to enable delivery of a shock to the patient either automatically, or semi-automatically when an operator (not shown) presses the shock button 30. Conversely, if analysis indicates that the patient is not suffering from a shockable heart rhythm, then the PU 114 effectively disables the shock button 30 by preventing the circuit 118 from delivering a shock to the patient when the operator presses the shock button 30.

Still referring to FIG. 8, the on/off switch 22 turns the AED 12 "on" and "off." The gate array 116 interfaces with the PM circuit 121, the on/off switch 22, and the status indicator 28, the circuit 118 for creating a defibrillation electrical shock, delivery, and ECG front-end, the PU 114, and the gate array 125.

The AED 12 also includes the display 24, which presents information to an operator, the speaker 26, which may provide audio instructions to the operator, and the microphone 32, which may record the operator's voice and other audible sounds. The data card 32 is coupled to the gate array 125 via a port 122, and may store the operator's voice and other sounds along with the patient's ECG and a record of AED events for later study.

A status-measurement circuit 124 provides the status of the other circuits of the AED 12 to the PU 114. LEDs 164 and the status indicator 28 provide information to the operator (not shown) such as whether the PU 114 has enabled the circuit 118 and the ECG front-end for creating and delivering a defibrillation electrical shock to the patient (not shown), or such as when the power supply 15 needs to be replaced. A contrast button 128 allows the operator to control the contrast of the display screen 24 if present, and a memory such as a read only memory (ROM) 130 stores programming information for the PU 114 and the gate arrays 116 and 125.

The AED 12 and other similar AED circuits that may incorporate the PM circuit 121 are discussed in the following references, which are incorporated by reference: U.S. Pat. No. 5,836,993 entitled ELECTROTHERAPY DEVICE CONTROL SYSTEM AND METHOD, U.S. Pat. No. 5,735,879 entitled ELECTROTHERAPY METHOD AND APPARATUS, U.S. Pat. No. 5,607,454 entitled ELECTROTHERAPY METHOD AND APPARATUS, and U.S. Pat. No. 5,879,374 entitled DEFIBRILLATOR WITH SELF-TEST FEATURES.

Figure 9:
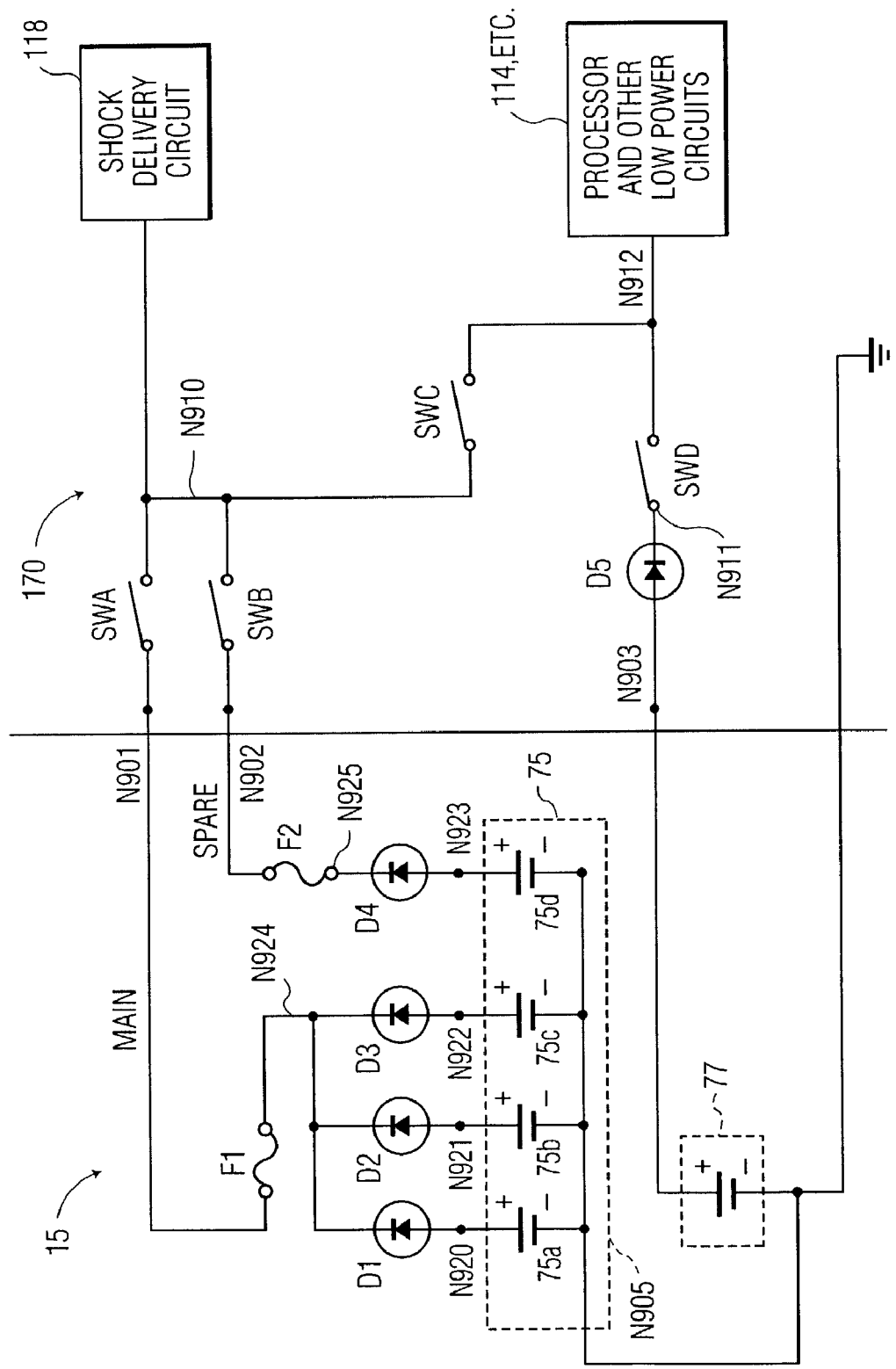
FIG. 9 is a schematic diagram of a portion of the power-management circuit of FIG. 8, according to an embodiment of the invention.

FIG. 9 is a schematic diagram of a circuit portion 170 of the power-management circuit 121 of FIG. 8, and a power-supply cassette 15 of FIG. 8, according to an embodiment of the invention. The cassette 15 includes high-power source 75 illustrated as batteries 75a–d, and low-power source 77 illustrated as batteries 77a–h (illustrated as a single cell). Diodes D1–D4, and fuses F1–F2 are included the cassette 15 for illustration, but alternatively may be included in the circuit portion 170. A divider line separates the diagram of FIG. 9 for illustrative purposes, but does not have a functional role.

The diodes D1–D4 have their anodes coupled to nodes N920–N923 respectively. The cathodes of diodes D1–D3 are coupled to the node N924, and the cathode of D4 is coupled to a node N925. A fuse F1 is coupled between the nodes N924 N901, and a fuse F2 is coupled between the nodes N925 and N902. The positive terminals of the batteries 75a–d are coupled to the nodes N920–N923 respectively, and the negative terminals are coupled to the node N905. The negative terminals of the batteries 77a–h (only one battery 77 is shown for clarity) are coupled to the node N905, and the positive terminals are coupled to the node N903.

One side of switches SWA–SWC is coupled to node N910. Another side of switch SWA is coupled to node N901, another side of switch SWB is coupled to node N902, and another side of switch SWC is coupled to node N912. Diode D5 has its anode coupled to node N903 and its cathode coupled to node N911. SWD is coupled between nodes N911 and N912. Node N905 is coupled to ground of the AED. The shock-delivery circuit 118 of FIG. 8 is coupled to the node N910. The shock-delivery circuit 118 generates the defibrillation shock, and may include delivery of the shock if required by the design of the AED. The processor 114 and other low-power circuits are coupled to the node N912, and include circuitry other than the circuitry generating the defibrillation shock.

In operation, the circuit portion 170 causes the battery 75 to power the high-power circuitry of the AED 12 such as the shock-delivery circuit 118 (FIG. 8), and causes the battery 77 to power the other circuitry including the processor 114. Specifically, while the AED 12 is not being used to resuscitate a patient (not shown), the processor 114 maintains the switches SWA, SWB, and SWC in an open position, and draws power from the battery 77 to perform self-tests and other similar functions. An exception to this is that during the portion of the self test where the processor measures the voltage across the battery 75, then the processor temporarily closes the switches SWA and SWC to measure the voltages across the batteries 75A–75C, then opens SWA and closes SWB to measure the voltage across the battery 75D. The processor 114 also measures the voltage across the battery 77. If the voltage across any of the batteries falls below a respective predetermined threshold, then the processor 114 can sound an alarm via the speaker 26, display 24, or LEDs 164 to notify someone that one or more of the batteries need to be replaced. Furthermore, if the processor 114 determines that the voltage across the battery 77 has fallen below its predetermined threshold, then in addition to sounding an alarm, it may close switches SWC and SWA so that it can receive power from the batteries 75A–75C until the battery 77 is replaced. This ensures that the AED 12 can function even if the battery 77 is discharged.

During operation when the AED 112 is used to resuscitate a patient (not shown), the processor 114 and other circuits continue to draw power from the battery 77. The processor 114 also closes the switch SWA, and, if necessary, SWB to allow the shock-delivery circuit 18 to charge up in preparation of delivering a defibrillation shock. Once the circuit 118 is charged up, the processor 114 can open the switches SWA and SWB, or can wait until the operator (not shown) is finished using the AED 12 to resuscitate a patient.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. An automated or semi-automated external defibrillator (AED) comprising:
high voltage circuitry which is operable for generating a defibrillation shock;
processor circuitry which is operable to control the AED;
monitoring circuitry for monitoring the condition of a power source; and a removable battery cassette having a cover which may be opened and closed, including one or more battery cells, located within the battery cassette and coupled to power the high voltage circuitry, the processor circuitry, and the monitoring circuitry, wherein the high voltage circuitry and the processor circuitry are located external to the battery cassette, and wherein at least one of the battery cells within the battery cassette can be accessed by opening the cover and replaced with another battery cell.

2. The AED of claim 1, wherein the battery cassette includes a first group of one or more battery cells coupled to power the high voltage circuitry and a second group of one or more battery cells coupled to power at least one of the processor circuitry and the monitoring circuitry.

3. The AED of claim 2, wherein the one or more battery cells of the first group can be replaced.

4. The AED of claim 2, wherein the one or more battery cells of the second group can be replaced.

5. The AED of claim 2, wherein the one or more battery cells of the first group and the one or more battery cells of the second group can be replaced.

6. The AED of claim 1, wherein the monitoring circuitry comprises monitoring circuitry which operates to monitor the condition of battery cells coupled to power the high voltage circuitry.

7. The AED of claim 6, wherein the monitoring circuitry is further operable to monitor the condition of battery cells coupled to power the monitoring circuitry and the processor circuitry.

8. The AED of claim 1:
wherein the monitoring circuitry comprises low voltage circuitry; and
wherein the battery cassette includes a cassette body and a first group of one or more battery cells coupled to power the high voltage circuitry to the exclusion of the low voltage circuitry and a second group of one or more battery cells coupled to power low voltage circuitry to the exclusion of the high voltage circuitry.

9. The AED of claim 8, wherein the second group of one or more battery cells comprise one or more replaceable batteries.

10. The AED of claim 9, wherein the one or more replaceable batteries comprise one or more alkaline batteries.

11. The AED of claim 8, wherein the first group of one or more battery cells comprise one or more lithium batteries.

12. An automated or semi-automated external defibrillator (AED) comprising:
high voltage circuitry which is operable for generating a defibrillation shock;
processor circuitry which is operable to control the AED;
monitoring circuitry for monitoring the condition of a battery; and
a removable battery cassette coupled to power the high voltage circuitry, the processor circuitry, and the monitoring circuitry,
wherein at least one of the monitoring circuitry and the processor circuitry comprises low voltage circuitry; and
wherein the battery cassette includes a cassette body and a plurality of battery cells of different battery chemistries located within the cassette body, for powering at least one of the processor and monitoring circuitry circuitry of the AED with one battery chemistry and the high voltage circuitry with a different battery chemistry.

13. The AED of claim 12, wherein the high voltage circuitry is powered by one or more batteries of a first battery chemistry and low voltage circuitry is powered by one or more batteries of a second battery chemistry.

14. The AED of claim 13, wherein the low voltage circuitry is powered by a removable alkaline battery.

15. The AED of claim 12, wherein the one or more batteries of the first battery chemistry are lithium batteries.

16. The AED of claim 15, wherein the one or more batteries of the second battery chemistry are alkaline batteries.

17. The AED of claim 12, wherein one of the battery cells in the battery cassette is a removable battery cell which powers low voltage circuitry of the AED; and
wherein the cover further comprises a sliding cover which slides open to allow removal of the removable battery cell.

18. An automated or semi-automated external defibrillator (AED) comprising:
high voltage circuitry which is operable for generating a defibrillation shock;
low voltage circuitry which performs an operating function of the AED;
a removable battery cassette including a cassette body with an operable cover and containing one or more batteries of a first battery type for powering the high voltage circuitry and one or more batteries of a second battery type for powering the low voltage circuitry,
wherein at least one of the batteries of the second battery type is removable from the cassette and may be accessed by opening the battery cassette cover and replaced with a new battery.

19. The AED of claim 18, wherein the replaceable battery comprises an alkaline battery.

20. The AED of claim 18, wherein the openable cover comprises a slide cover which slides open and closed.

21. The AED of claim 18, wherein the first and second battery types comprise batteries of different battery chemistries.

22. The AED of claim 18, wherein the low voltage circuitry operating function comprises a monitoring function.

23. The AED of claim 22, wherein the monitoring function includes a self-test function.

* * * * *